United States Patent
Prokopova et al.

(10) Patent No.: US 11,786,526 B2
(45) Date of Patent: Oct. 17, 2023

(54) PHARMACEUTICAL COMPOSITION COMPRISING ROSUVASTATIN AND EZETIMIBE AND A PREPARATION METHOD THEREOF

(71) Applicant: SANOFI, Paris (FR)

(72) Inventors: Alena Prokopova, Prague (CZ); Jaroslava Svobodova, Krenice (CZ); Ondrej Dammer, Hostivice (CZ); Petr Mikes, Prague (CZ)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 16/330,268

(22) PCT Filed: Aug. 31, 2017

(86) PCT No.: PCT/CZ2017/050037
§ 371 (c)(1),
(2) Date: Mar. 4, 2019

(87) PCT Pub. No.: WO2018/041282
PCT Pub. Date: Mar. 8, 2018

(65) Prior Publication Data
US 2020/0009136 A1  Jan. 9, 2020

(30) Foreign Application Priority Data
Sep. 5, 2016 (CZ) .............................. PV 2016-539

(51) Int. Cl.
| | | |
|---|---|---|
| *A61K 31/505* | (2006.01) | |
| *A61K 9/20* | (2006.01) | |
| *A61K 9/24* | (2006.01) | |
| *A61K 9/28* | (2006.01) | |
| *A61K 31/397* | (2006.01) | |

(52) U.S. Cl.
CPC ............ *A61K 31/505* (2013.01); *A61K 9/209* (2013.01); *A61K 9/2018* (2013.01); *A61K 9/2813* (2013.01); *A61K 31/397* (2013.01)

(58) Field of Classification Search
None
See application file for complete search history.

(56) References Cited

U.S. PATENT DOCUMENTS

| | | | | |
|---|---|---|---|---|
| 2005/0281873 | A1* | 12/2005 | Badwan | A61K 31/522 424/468 |
| 2014/0287042 | A1* | 9/2014 | Dias | A61K 31/505 424/465 |

FOREIGN PATENT DOCUMENTS

| | | |
|---|---|---|
| CN | 103 585 157 B | 2/2016 |
| CN | 105310993 A | 2/2016 |
| JP | 2012-504155 A | 2/2012 |
| MX | 2012 014 970 A | 8/2013 |
| WO | WO 2010/037728 A2 | 4/2010 |
| WO | WO 2012/064307 A1 | 5/2012 |
| WO | WO 2013/166117 A1 | 11/2013 |
| WO | WO 2015/044698 A2 | 4/2015 |
| WO | WO 2015/102400 A1 | 7/2015 |
| WO | WO 2015/199356 A1 | 12/2015 |
| WO | WO 2009/024889 A2 | 2/2022 |

OTHER PUBLICATIONS

International Search Report and Written Opinion dated Nov. 23, 2017 in related PCT Application No. PCT/CZ2017/050037 filed Aug. 31, 2017 (10 pages).

* cited by examiner

*Primary Examiner* — Jake M Vu
(74) *Attorney, Agent, or Firm* — LATHROP GPM LLP; James H. Velema, Esq.

(57) ABSTRACT

The invention relates to a pharmaceutical composition comprising the active ingredients rosuvastatin of formula I, with the systematic name (3R,5S,6E)-7-[4-(4-fluorophenyl)-2-(N-methylmethanesulfonamido)-6-(propan-2-yl)pyrimidin-5-yl]-3,5-dihydroxyhept-6-enoic acid or its pharmaceutically acceptable salts, esters, hydrates or solvates, and ezetimibe of formula II, with the systematic name (3R,4S)-1-(4-fluorophenyl)-3-[(3S)-3-(4-fluorophenyl)-3-hydroxypropyl]-4-(4-hydroxyphenyl)azetidin-2-one or its pharma- (Continued)

ceutically acceptable salts, esters, hydrates or solvates, as well as a preparation method of this pharmaceutical composition. The weight ratio of the layers is 1:2 to 2:1.
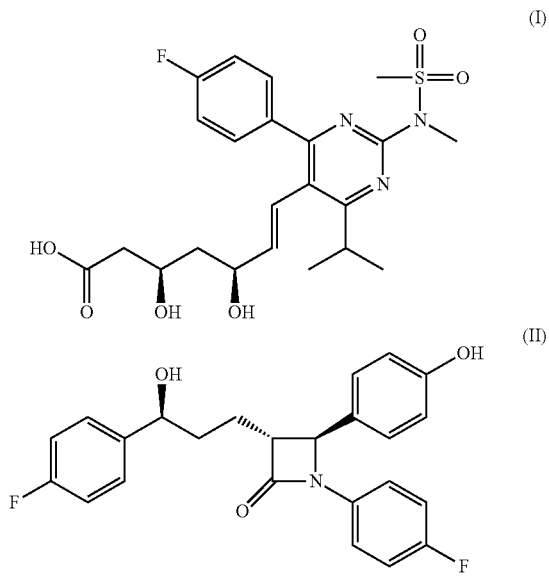
15 Claims, 1 Drawing Sheet

PHARMACEUTICAL COMPOSITION COMPRISING ROSUVASTATIN AND EZETIMIBE AND A PREPARATION METHOD THEREOF

CROSS-REFERENCE TO RELATED APPLICATIONS

This application is a 35 U.S.C. § 371 filing of International Patent Application No. PCT/CZ2017/050037, filed Aug. 31, 2017, which claims priority to Czech Republic Patent Application No. PV 2016-539, filed Sep. 5, 2016, the entire contents of which are incorporated herein by reference.

FIELD OF THE INVENTION

An object of the invention is a pharmaceutical composition comprising the active ingredients rosuvastatin of formula I, with the systematic name (3R,5S,6E)-7-[4-(4-fluorophenyl)-2-(N-methylmethanesulfonamido)-6-(propan-2-yl)pyrimidin-5-yl]-3,5-dihydroxyhept-6-enoic acid or its pharmaceutically acceptable salts, and ezetimibe of formula II, with the systematic name (3R,4S)-1-(4-fluorophenyl)-3-[(3S)-3-(4-fluorophenyl)-3-hydroxypropyl]-4-(4-hydroxyphenyl)azetidin-2-one or its pharmaceutically acceptable salts, as well as a method for preparation of this pharmaceutical composition.

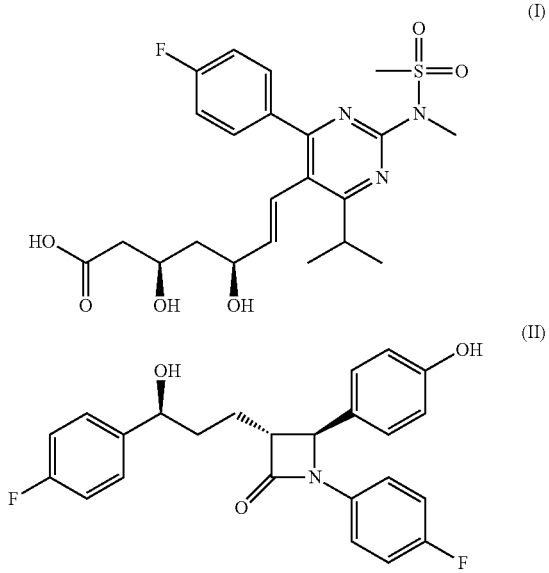

BACKGROUND ART

Rosuvastatin or a pharmaceutically acceptable salt thereof is one of HMG-CoA reductase inhibitors that inhibit the synthesis of cholesterol to treatment dyslipidaemia. Crestor® tablets (rosuvastatin calcium salts developed by AstraZeneca), including rosuvastatin as a main ingredient, have been widely used for the treatment of dyslipidaemia and dyslipidaemia-related disorders. In particular, research has been reporting on excellent effects of rosuvastatin in lowering LDL cholesterol levels in blood and increasing beneficial HDL cholesterol levels in the body, compared to the effects of atorvastatin or simvastatin, which is commercially available as a drug having the same mechanism as rosuvastatin. Accordingly, there is an increasing interest in rosuvastatin formulation.

Ezetimibe (Ezetrol® tablets, Merck & Co.) is a selective cholesterol absorption inhibitor. HMG-CoA reductase inhibitors are generally used in a combination with a therapeutic agent for dyslipidemia having a different mechanism from that of the HMG-CoA reductase inhibitors to enhance therapeutic effects. Among such combinations, due to good drug interaction between the HMG-CoA reductase inhibitor and ezetimibe as a drug inhibiting the re-absorption of cholesterol in the small intestine, composite formulations of these two ingredients are actively being studied.

Through much research, combined treatment of ezetimibe with rosuvastatin is also reported as having excellent pharmaceutical effects. Rosuzet® composite pack, containing both Ezetrol® (ezetimibe) and MSD rosuvastatin tablets, was developed by Merck & Co. for the treatment of primary hypercholesterolemia. Viazet® hard capsules, containing ezetimibe and rosuvastatin zinc, were developed by EGIS Pharmaceuticals PLC for the treatment of primary hypercholesterolemia. In order to prepare an effective fixed-dose formulation in a tablet form, it is necessary to ensure high bioavailability of the active ingredients. A dissolution pattern of the active ingredients of a solid formulation for oral administration is closely related to the bioavailability of the formulation, wherein high dissolution rate is premised on high bioavailability.

WO2009024889 (Ranbaxy Laboratories) relates generally to combinations of HMG-CoA reductase inhibitors with ezetimibe and deals with the problem of degradation of ezetimibe in the presence of alkali metal salt additives. The issue is solved by addition of alkaline earth metal additives instead.

WO2011019326 (Bilgic Mahmut) relates to a process for preparation of a pharmaceutical formulation comprising ezetimibe and rosuvastatin. The said process includes dissolution of ezetimibe and preparation of ezetimibe by wet granulation. The examples of such formulations include only monolayer compositions comprising a phosphate and microcrystalline cellulose among other excipients.

WO2012064307 (Bilgic Mahmut) discloses rosuvastatin or its pharmaceutically acceptable salt formulations wherein the rosuvastatin particle size distribution $d_{(0.90)}$ is coarser than 100 μm. The composition of the bilayer tablet is not disclosed sufficiently to be prepared by a person skilled in the art.

WO2013066279 (Bilgic Mahmut) discloses examples of pharmaceutical formulations comprising ezetimibe and/or pharmaceutically acceptable salt thereof with a second active ingredient wherein the particle size of ezetimibe is between 10 to 50 μm.

WO2013166117 (Althera Life Sciences) discloses examples of solid dosage formulations comprising combinations of ezetimibe and rosuvastatin in one tablet that is expected to have the same area under curve (AUC) as the two active ingredients taken individually orally. This patent application solves the issue of rosuvastatin degradation by addition of a basic milieu to the rosuvastatin layer; particularly the addition of dicalcium phosphate is mentioned. The process for preparation of the ezetimibe layer is very complex and thus also cost-demanding: two steps out of the five require usage of solvents (organic solvents and water, respectively), each of them followed by energy demanding drying. Furthermore, the proposed "mounting" of ezetimibe solution on lactose surface under very restricting and specific conditions makes the proposed process ineffective and not robust enough.

WO2015044698 (Egis Pharmaceuticals) discloses examples of combined ezetimibe and rosuvastatin pharmaceutical composition wherein the interaction with the individual active ingredients is minimized. The solution to such a problem is a capsule containing a tablet comprising rosuvastatin zinc salt (2:1) and a tablet comprising ezetimibe.

WO2015102400 (HANMI Pharm. Co.) discloses examples of ezetimibe and rosuvastatin compositions in a form of a single-layered or a double-layered tablet or capsules. The only example of a double-layered tablet is a composition containing ezetimibe and rosuvastatin wherein the ezetimibe part of the composition includes magnesium stearate in the concentration of 1.3 wt. %.

WO2015199356 (HANMI Pharm. Co.) relates to a composite formulation including ezetimibe and rosuvastatin having improved dissolution rate and velocity of active ingredients. The main invention is the critical content of organic solvent for the preparation of ezetimibe wet-granules.

An object of the present invention is preparation of a stable two-layer tablet comprising as the active ingredients rosuvastatin or its pharmaceutically acceptable salts and ezetimibe or its pharmaceutically acceptable salts.

DISCLOSURE OF THE INVENTION

The invention relates to a stable pharmaceutical composition comprising, as the active ingredients, rosuvastatin or its pharmaceutically acceptable salts, hydrates, solvates or esters, and ezetimibe or its pharmaceutically acceptable salts, hydrates, solvates or esters, the pharmaceutical composition according to the invention having the form of a two-layer tablet wherein each layer of the tablet only contains one of these active ingredients.

According to the invention, the weight ratio of the rosuvastatin layer and the ezetimibe layer of the two-layer tablet is preferably 1:2 to 2:1, including the limit values.

According to the invention, the ezetimibe layer preferably contains 0.15 to 0.5% by weight of a glidant, relative to the total weight of the ezetimibe layer, said glidant being preferably selected from stearic acid or its pharmaceutically acceptable salts.

According to the invention, the ezetimibe layer is preferably free of cellulose and its derivatives, i.e., the ezetimibe layer comprises other pharmaceutically acceptable excipients than cellulose and its derivatives. In another embodiment, the ezetimibe layer comprises cellulose and/or its derivatives (preferably microcrystalline cellulose) in an amount of up to 10.5% by weight, incl. the limit values, relative to the total weight of the ezetimibe layer, whereas the cellulose and/or its derivatives are present in the extragranular phase only.

According to the invention, the rosuvastatin layer is free of basic stabilizing excipients.

Another object of the invention is a robust production method of such a composition.

DETAILED DESCRIPTION OF THE INVENTION

An object of the invention is a pharmaceutical composition comprising rosuvastatin of formula I, with the systematic name (3R,5S,6E)-7-[4-(4-fluorophenyl)-2-(N-methyl-methanesulfonamido)-6-(propan-2-yl)pyrimidin-5-yl]-3,5-dihydroxyhept-6-enoic acid or its pharmaceutically acceptable salts, hydrates, solvates or esters, and ezetimibe of formula II, with the systematic name (3R,4S)-1-(4-fluorophenyl)-3-[(3S)-3-(4-fluorophenyl)-3-hydroxypropyl]-4-(4-hydroxyphenyl)azetidin-2-one or its pharmaceutically acceptable salts, hydrates, solvates or esters, and pharmaceutically acceptable excipients, characterized in that it is in the form of a two-layer tablet with one layer comprising ezetimibe as the only active ingredient and one layer comprising rosuvastatin as the only active ingredient.

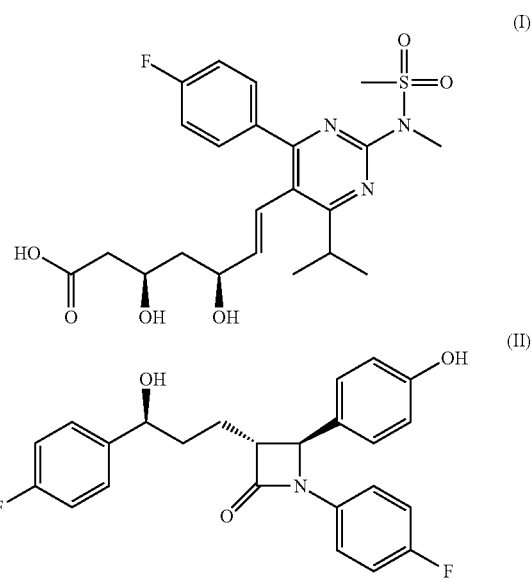

An advantage of the two-layer tablet is separation of individual ingredients, which prevents their interaction and also allows to independently adapt each tablet layer to the physicochemical characteristics of individual active ingredients. Thus, independent and free releasing of ezetimibe and rosuvastatin from individual layers of the tablet can be ensured. The two-layer tablets according to individual aspects of the present invention show further improved physico-chemical properties.

In this text and unless indicated otherwise, the term "ezetimibe" refers to ezetimibe or its pharmaceutically acceptable inorganic or organic salt, ester, hydrate, solvate, enantiomer, racemate, polymorph, crystalline form and amorphous form and/or combination thereof. According to one aspect of the invention, a two-layer tablet preferably contains the amount corresponding to 10 mg of free ezetimibe, i.e. ezetimibe that is not in the form of an inorganic or organic salt, ester, hydrate or solvate.

In this text and unless indicated otherwise, the term "rosuvastatin" refers to rosuvastatin or its pharmaceutically acceptable inorganic or organic salt, ester, hydrate, solvate, enantiomer, racemate, crystalline form and amorphous form and/or combination thereof. Among the pharmaceutically acceptable salts, inorganic salts, e.g. calcium, magnesium, sodium, potassium, lithium, zinc, copper, manganese or cadmium salts are preferred. Calcium, magnesium, zinc and copper salts are especially preferred, with the calcium and magnesium salts being most preferred, especially the calcium salt. One two-layer tablet according to the invention preferably contains the amount corresponding to 2.5-40 mg of free rosuvastatin, i.e. rosuvastatin that is not in the form of an inorganic or organic salt, ester, hydrate or solvate.

The term "ezetimibe layer" refers to one of the two layers of the two-layer tablet that contains the active substance ezetimibe as the only active substance in this layer, and pharmaceutically acceptable excipients.

Preferably, the ezetimibe layer comprises a glidant selected from the group consisting of stearic acid or its acceptable salts, which is used in the ezetimibe layer at a concentration of 0.15 to 0.5% by weight, relative to the total weight of this layer.

Preferably, the ezetimibe layer may contain at least one pharmaceutically acceptable excipient selected from:
 a filler or a combination of fillers selected from the group of lactose, glucose, cellulose and its derivatives, calcium carbonate, calcium phosphate, starch, mannitol and other sugar alcohols, and other fillers known from the prior art,
 a disintegrant or a combination of disintegrants selected from the group of the sodium salt of croscarmellose, sodium salt of carboxymethyl starch, crospovidone and alginates,
 a binder or a combination of binders selected from the groups of water-soluble polymers such as polyvinylpyrrolidone, preferably polyvinylpyrrolidone with the average molecular weight up to 1,500,000, preferably up to 60,000, water-soluble cellulose derivatives, preferably methylcellulose, hydroxyethyl cellulose, hydroxypropyl cellulose, hydroxypropyl methylcellulose, sugar alcohols, preferably mannitol, sorbitol,
 a surfactant or a combination of surfactants selected from the group of block copolymers of ethylene oxide and propylene oxide (referred to as poloxamers, where the term "poloxamer" means a polymer of formula $HO(C_2H_4)_a(C_3H_6O)_b(C_2H_4O)_aH$, wherein "a" and "b" indicate the number of oxyethylene and oxypropylene units), alkyl sulphates, preferably sodium lauryl sulphate, sodium stearyl sulphate, sodium dioctyl sulfosuccinate, alkyl aryl sulfonates, preferably sodium dodecyl benzene sulfonate, polyethylene glycols and polysorbates.

Preferably, the ezetimibe layer comprises at least one first pharmaceutically acceptable excipient and at least one second pharmaceutically acceptable excipient.

More preferably, the ezetimibe layer comprises a granulate comprising ezetimibe and at least one first pharmaceutically acceptable excipient, and an extragranular phase comprising at least one second pharmaceutically acceptable excipient.

Preferably, the second pharmaceutically acceptable excipients include a glidant selected from the group consisting of stearic acid or its pharmaceutically acceptable salts, in an amount of 0.15 to 0.5% by weight, relative to the total weight of the ezetimibe layer.

In a preferred embodiment, the ezetimibe layer comprises a granulate and an extragranular phase, wherein the granulate is substantially free of cellulose and its derivatives. The extragranular phase may be free of cellulose and its derivatives, or may contain cellulose and/or its derivatives in an amount of up to 10.5% by weight, incl. the limit values, relative to the weight of the ezetimibe layer. I.e., the ezetimibe layer either comprises other pharmaceutically acceptable excipients than cellulose and its derivatives, or it comprises cellulose and/or its derivatives (preferably microcrystalline cellulose) at a concentration up to 10.5% by weight, incl. the limit values, relative to the weight of the ezetimibe layer, in the extragranular phase only.

The term "rosuvastatin layer" refers to one of the two layers of the two-layer tablet that contains the active substance rosuvastatin as the only active substance in this layer, preferably in an amount corresponding to 2.5-40 mg of rosuvastatin, and at least one pharmaceutically acceptable excipient. The rosuvastatin layer is preferably free of basic stabilizing excipients.

The pharmaceutically acceptable non-basic excipients in the rosuvastatin layer may include:
 a filler or a combination of fillers selected from the group of lactose, glucose, cellulose and its derivatives, starch, mannitol and other sugar alcohols, and other non-basic fillers known from the prior art,
 a binder or a combination of binders selected from the group of water-soluble polymers such as polyvinylpyrrolidone, preferably polyvinylpyrrolidone with the average molecular weight of up to 1,500,000, preferably up to 60,000, water-soluble cellulose derivatives, preferably methylcellulose, hydroxyethyl cellulose, hydroxypropyl cellulose, hydroxypropyl methylcellulose, sugar alcohols, preferably mannitol, sorbitol,
 a glidant or a combination of glidants such as colloidal silicon dioxide, maize starch, magnesium or calcium stearate, stearic acid, sodium stearyl fumarate, talc, polyethylene oxide and other glidants known from the prior art,
 a disintegrant or a combination of disintegrants selected from the group of the sodium salt of croscarmellose, sodium salt of carboxymethyl starch, crospovidone and alginates.

"Basic stabilizing excipients" are excipients which, after dispersing the pharmaceutical composition in an aqueous environment, increase the pH value above pH 9. Such substances include e.g. carbonates such as calcium carbonate, hydroxides of alkaline metals and alkaline earth metals such as calcium hydroxide, calcium phosphate, or calcium hydrogen phosphate, basic amino acids or meglumine.

The definitions of the ezetimibe layer and the rosuvastatin layer inherently indicate that the claimed "two-layer tablet" consists of an ezetimibe layer and a rosuvastatin layer. This two-layer tablet can be preferably coated. The coating of the tablets then comprises film-forming substances such as hydroxypropyl methylcellulose, methylcellulose, polyvinyl alcohol, and optionally other excipients selected from the group of softeners such as e.g. triethyl citrate, dibutyl sebacate, or polyethylene glycol, surfactants such as e.g. sodium lauryl sulphate, colorants such as e.g. iron oxides and titanium dioxide, and additives preventing sticking of tablets, e.g. talc. If the text refers to a "tablet", it is to be understood as referring to the "two-layer tablet" according to the invention.

The references to Ph. Eur. or European Pharmacopoeia relate more specifically to its $9^{th}$ Edition (released in 2016, version 9.0).

The term "stable formulation" and/or "stable two-layer tablet" refers to such a formulation and/or tablet that, subjected to a stability test, contains
 less than 1% by weight, preferably less than 0.7% by weight, most preferably less than 0.55% by weight of impurities derived from rosuvastatin, relative to the declared quantity of rosuvastatin, and
 less than 1% by weight, preferably less than 0.5% by weight, most preferably less than 0.2% by weight of impurities derived from ezetimibe, relative to the declared quantity of ezetimibe.

In this text and unless indicated otherwise, the term "particle size $d_{(x)}$" means that 100× x % of the particle volume have a diameter that is smaller than, larger than or equal, respectively, to the said diameter value d, measured with the laser scattering method. I.e. if e.g. $d_{(0.90)}$ of rosuvastatin is larger than 100 μm, it means that 90% of the volume of particles of rosuvastatin or its pharmaceutically acceptable salt are larger than 100 μm, measured with the laser scattering method. Conversely, if e.g. the particle size $d_{(0.90)}$ is equal to or smaller than 15 μm, it means that 90% of the volume of particles of ezetimibe or its pharmaceutically acceptable salt are equal to or smaller than 15 μm, measured with the laser scattering method.

Preferably, $d_{(0.90)}$ of ezetimibe is smaller than or equal to 25 μm, more preferably $d_{(0.90)}$ is smaller than or equal to 20 μm and most preferably $d_{(0.90)}$ is smaller than or equal to 15 μm, measured with the laser scattering method.

Preferably, $d_{(0.90)}$ of rosuvastatin is in the range of 100-225 μm, more preferably $d_{(0.90)}$ is in the range of 130-200 μm and most preferably $d_{(0.90)}$ is in the range of 150-175 μm, measured with the laser scattering method.

During the development of a two-layer tablet containing the active ingredients rosuvastatin and ezetimibe, it was observed that during production, breaking or crushing of the tablet layers occurred, or a large proportion of tablets fell apart into individual layers during further processing. Also observed was an undesired variability of the average contents of the active ingredients in individual layers as well as lack of uniformity of the contents, and these two parameters did not comply with the requirements as defined by the European Pharmacopoeia. As documented by the Examples, the efficiency and robustness of the production process turned out to depend on the weight ratio between the ezetimibe layer and rosuvastatin layer.

Testing of various ratios showed that this technological problem was solved if the weight ratio of individual layers was adjusted to a value in the range of 1:2 to 2:1 (including the limit values). Such tablets manifested abrasion, determined using the method according to the European Pharmacopoeia, of less than 0.2%.

Another problem that needed to be solved within the framework of the development of the two-layer tablet of ezetimibe and rosuvastatin consisted in achieving a sufficient release rate of ezetimibe from the tablet. Ezetimibe is almost insoluble in water, which reduces the dissolution rate in an aqueous environment, e.g. also in the digestive juices. This may result in low biological availability of ezetimibe, i.e. its insufficient efficiency. Therefore, developing a formulation providing high biological availability of ezetimibe and a high release rate of ezetimibe from the tablet is highly desirable for the pharmaceutical industry.

Glidants such as stearic acid and its salts have a negative impact on release rate of active ingredients from pharmaceutical formulations. Glidants repel water, reducing the rate of dissolution of active ingredients from the formulation. Reference literature indicates that stearic acid or its pharmaceutically acceptable salts, preferably magnesium stearate and aluminum stearate, can be used in pharmaceutical formulations in a quantity of 0.2 to 2% by weight. However, it is well known from the prior art that the usual content of stearic acid or its pharmaceutically acceptable salt, preferably magnesium stearate, calcium stearate and/or aluminum stearate, for a pharmaceutical technological process, is approx. 1% by weight or higher for the tablets to be preparable at all. If an insufficient amount of glidants is used, technological problems can be expected during the production of tablets, such as sticking of the material to the punch or in the mold.

It has been surprisingly found that a sufficient amount of stearic acid or its pharmaceutically acceptable salt, preferably magnesium stearate, calcium stearate and/or aluminum stearate, in the ezetimibe layer for the production of two-layer tablets in accordance with the invention is from 0.15 to 0.5% by weight (including the limit values, relative to the total weight of the ezetimibe layer). A low content of stearic acid or its pharmaceutically acceptable salts, preferably magnesium stearate, calcium stearate and/or aluminum stearate, is advantageous for faster dissolution and release of ezetimibe from the tablet.

Thus, this invention of a two-layer tablet brings the above-described advantages of a low content of a glidant, which is stearic acid or its acceptable salt, preferably magnesium stearate, calcium stearate and/or aluminum stearate, in the ezetimibe layer for the releasing of ezetimibe, and at the same time, these tablets are easy to prepare in spite of the low content of the glidant.

Cellulose and its derivatives, especially microcrystalline cellulose, also have an impact on release rate of ezetimibe from the tablet. Testing of many varieties (Comparative Example C being provided for illustration) has shown that the presence of cellulose and its derivatives, especially microcrystalline cellulose, in the intragranular phase of the ezetimibe layer decelerates releasing of ezetimibe from the tablet. Cellulose and its derivatives can be used in the extragranular phase, but only at a concentration of up to 10.5% by weight, including the limit values, relative to the weight of the ezetimibe layer, an extreme and advantageous embodiment being represented by a two-layer tablet whose ezetimibe layer does not comprise any cellulose or cellulose derivatives.

The two-layer oral tablet according to the invention is thus characterized in that the ezetimibe layer comprises other pharmaceutically acceptable excipients than cellulose and its derivatives. Alternatively, the ezetimibe layer may comprise cellulose and its derivatives, preferably microcrystalline cellulose, at a concentration of up to 10.5% by weight, incl. the limit values, relative to the weight of the ezetimibe layer, in the extragranular phase only.

More than 85% by weight of the declared content of ezetimibe are released from the two-layer tablets according to the invention during 30 min in dissolution tests. In a preferred embodiment, more than 90% by weight of the declared content of ezetimibe, and in an especially preferred embodiment, more than 95% of the declared content of ezetimibe is released during 30 min in dissolution tests.

More than 75% by weight of the declared content of ezetimibe are released from the two-layer tablets according to the invention during 20 min in dissolution tests. In a preferred embodiment, more than 80% by weight of the declared content of ezetimibe and in an especially preferred embodiment, more than 86% of the declared content of ezetimibe is released during 20 min in dissolution tests.

The third aspect of the present invention is the absence of basic excipients in the rosuvastatin layer. It is well-known from reference sources that rosuvastatin and its salts are unstable in an acidic environment. Therefore, for stabilization of pharmaceutical formulations of rosuvastatin, reference sources recommend the use of basic stabilizing substances such as calcium carbonate, calcium hydroxide, or phosphates, especially calcium hydrogen phosphate, which is contained in the commercial preparation of rosuvastatin Crestor®.

However, dissolution of a formulation containing basic stabilizing excipients can unnaturally increase the normal acidic pH in the stomach, which has an unfavorable impact on the mucous membrane of the stomach. This impact is especially negative for patients suffering from diseases of the stomach and stomach wall, special caution being necessary in patients with long-term rosuvastatin therapy. The presence of basic substances in the formulation can also have a negative influence on stability and dissolution of ezetimibe from a common formulation of ezetimibe and rosuvastatin.

During the development and comparative tests it was surprisingly found that for the two-layer tablet according to the invention it was not necessary to use basic stabilizing substances in the rosuvastatin layer.

In a preferred embodiment, the two-layer tablet comprises, in the ezetimibe layer, a granulate of ezetimibe with lactose, sodium salt of croscarmellose and/or sodium salt of carboxymethyl starch, sodium lauryl sulfate and/or sodium lauryl stearate, and hydroxypropyl methylcellulose and/or polyvinylpyrrolidone with a molecular weight of less than 60,000. In a preferred embodiment, the two-layer tablet contains, in the ezetimibe layer, an extragranular phase with 0.15 to 0.5% by weight of magnesium stearate or calcium stearate or aluminum stearate (relative to the weight of the ezetimibe layer), sodium salt of croscarmellose and/or sodium salt of carboxymethyl starch, and optionally microcrystalline cellulose at a concentration of up to 10.5% by weight (relative to the weight of the ezetimibe layer).

In a preferred embodiment, the two-layer tablet comprises, in the rosuvastatin layer: rosuvastatin, lactose, microcrystalline cellulose, sodium salt of croscarmellose and/or sodium salt of carboxymethyl starch, colloidal silicon dioxide, and magnesium stearate and/or calcium stearate and/or aluminum stearate.

In an especially preferred embodiment, the two-layer tablet contains, in the ezetimibe layer, granulate of ezetimibe with lactose, sodium salt of croscarmellose, sodium lauryl sulphate and polyvinylpyrrolidone with a molecular weight of less than 35,000, and an extragranular phase comprising 0.15 to 0.5% by weight of magnesium stearate (related to the weight of the ezetimibe layer), sodium salt of croscarmellose, and optionally microcrystalline cellulose at a concentration of up to 10.5% by weight (relative to the weight of the ezetimibe layer).

In an especially preferred embodiment, the two-layer tablet comprises, in the rosuvastatin layer: rosuvastatin, lactose, microcrystalline cellulose, sodium salt of croscarmellose, colloidal silicon dioxide and magnesium stearate.

The tablet in accordance with the present invention can be produced with the use of methods that are known to a skilled person.

The tableting blend for the production of the ezetimibe layer is preferably prepared using known granulation methods, wet granulation being preferred. The tableting blend for the production of the rosuvastatin method can be preferably prepared using dry methods, direct mixing and direct compression being preferred. A preferred production process is the combination of wet granulation for the ezetimibe layer and direct mixing and compression for the rosuvastatin layer. The composition of the rosuvastatin layer according to the invention, which enables the use of direct mixing and compression, is very advantageous from the point of view of time and economy. The ratio of pressures for compression of the tableting blends into the two-layer tablet is preferably 1:2 to 1:10, the first value relating to the pressure for compression of the first layer (typically the layer with a higher thickness) and the second value relating to the pressure for compression of the second layer and the whole tablet.

The disintegration time of the two-layer tablets according to the invention is less than 15 min, preferably less than 8 min, most preferably less than 5 min, measured with the method according to the European Pharmacopoeia. The strength of the two-layer tablets according to the invention is at least 60 N, preferably more than 110 N and most preferably more than 140 N, measured with the method according to the European Pharmacopoeia.

The tablet in accordance with the present invention can be prepared by means of a production process comprising the following steps:
 a) ezetimibe or its pharmaceutically acceptable salt, together with at least one first pharmaceutically acceptable excipient, is granulated, preferably with the use of a wetting agent,
 b) the obtained granules of ezetimibe are mixed with at least one second pharmaceutically acceptable excipient,
 c) rosuvastatin or its pharmaceutically acceptable salt, is mixed together with at least one pharmaceutically acceptable excipient, wherein the pharmaceutically acceptable excipient(s) are non-basic,
 d) the obtained tableting blend of ezetimibe and rosuvastatin is compressed into two-layer tablets,
 e) coating is optionally applied onto the obtained two-layer tablets.

A preferred embodiment comprises a preparation method wherein a mixture of ezetimibe with at least one first pharmaceutically acceptable excipient in step a) is wetted with the use of water and the obtained mixture is processed into granulate by means of fluid granulation. The at least one first pharmaceutically acceptable excipient in step a) is selected from a group comprising a filler, a binder, a disintegrant, a surfactant or any combinations thereof, as described above.

In a preferred embodiment, the at least one second excipient in step b) is a glidant selected from the group consisting of stearic acid or its acceptable salts, which is used in the ezetimibe layer at a concentration of 0.15 to 0.5% by weight, relative to the total weight of this layer, and optionally further excipients, such as a filler, a binder or a disintegrant or a combination of these substances, as described above.

In a preferred embodiment, the at least one second excipient in step b) can include microcrystalline cellulose at a concentration of up to 10.5% by weight (relative to the weight of the ezetimibe layer).

As the pharmaceutically acceptable excipients, the rosuvastatin layer can comprise at least one pharmaceutically acceptable non-basic excipient as defined in the above-described "rosuvastatin layer". The first pharmaceutically acceptable excipient and the second pharmaceutically acceptable excipients are as defined in the above-described "ezetimibe layer".

Individual preferred aspects of the invention are the following embodiments:

1. A two-layer tablet comprising, as the active ingredients, rosuvastatin or its pharmaceutically acceptable salts, esters, hydrates or solvates, and ezetimibe or its pharmaceutically acceptable salts, esters, hydrates or solvates, wherein each tablet layer only contains one of these active substances and the weight ratio of the individual layers is 1:2 to 2:1 (including the limit values).

2. A two-layer tablet comprising, as the active ingredients, rosuvastatin or its pharmaceutically acceptable salts, esters, hydrates or solvates, and ezetimibe or its pharmaceutically acceptable salts, esters, hydrates or solvates, wherein the ezetimibe layer comprises 0.15 to 0.5% by weight of a glidant, which is stearic acid or its acceptable salts.

3. A two-layer tablet comprising, as the active ingredients, rosuvastatin or its pharmaceutically acceptable salts, esters, hydrates or solvates, and ezetimibe or its pharmaceutically acceptable salts, esters, hydrates or solvates, wherein the ezetimibe layer is substantially free of cellulose and its derivatives, or wherein the ezetimibe layer comprises cellulose and its derivatives in the extragranular phase only (preferably microcrystalline cellulose) at a concentration of up to 10.5% by weight, incl. the limit values, relative to the weight of the ezetimibe layer.

4. A two-layer tablet comprising as the active ingredients rosuvastatin or its pharmaceutically acceptable salts, esters, hydrates or solvates, and ezetimibe or its pharmaceutically acceptable salts, esters, hydrates or solvates, wherein the rosuvastatin layer is substantially free of basic stabilizing excipients.

5. A two-layer tablet comprising, as the active ingredients, rosuvastatin or its pharmaceutically acceptable salts, esters, hydrates or solvates, and ezetimibe or its pharmaceutically acceptable salts, esters, hydrates or solvates, wherein each tablet layer only contains one of these active substances and the weight ratio of the individual layers is 1:2 to 2:1 (including the limit values), and wherein the ezetimibe layer comprises a glidant, which is stearic acid or its acceptable salts, at a concentration of 0.15 to 0.5% by weight, relative to the weight of the ezetimibe layer.

6. A two-layer tablet comprising, as the active ingredients, rosuvastatin or its pharmaceutically acceptable salts, esters, hydrates or solvates, and ezetimibe or its pharmaceutically acceptable salts, esters, hydrates or solvates, wherein each tablet layer only comprises one of these active substances and the weight ratio of the individual layers is 1:2 to 2:1 (including the limit values), and wherein the ezetimibe layer is substantially free of cellulose and its derivatives, or wherein the ezetimibe layer comprises cellulose and its derivatives in the extragranular phase only (preferably microcrystalline cellulose) at a concentration of up to 10.5% by weight, incl. the limit values, relative to the weight of the ezetimibe layer.

7. A two-layer tablet comprising, as the active ingredients, rosuvastatin or its pharmaceutically acceptable salts, esters, hydrates or solvates, and ezetimibe or its pharmaceutically acceptable salts, esters, hydrates or solvates, wherein each tablet layer only contains one of these active substances and the weight ratio of the individual layers is 1:2 to 2:1 (including the limit values), and wherein the rosuvastatin layer is substantially free of basic stabilizing excipients.

8. A two-layer tablet comprising, as the active ingredients, rosuvastatin or its pharmaceutically acceptable salts, esters, hydrates or solvates, and ezetimibe or its pharmaceutically acceptable salts, esters, hydrates or solvates, wherein each tablet layer only contains one of these active substances and the weight ratio of the individual layers is 1:2 to 2:1 (including the limit values), and wherein the ezetimibe layer comprises a glidant, which is stearic acid or its acceptable salts, at a concentration of 0.15 to 0.5% by weight, relative to the weight of the ezetimibe layer, and wherein the ezetimibe layer is substantially free of cellulose and its derivatives, or wherein the ezetimibe layer comprises cellulose and its derivatives in the extragranular phase only (preferably microcrystalline cellulose) at a concentration of up to 10.5% by weight, incl. the limit values, relative to the weight of the ezetimibe layer.

9. A two-layer tablet comprising, as the active ingredients, rosuvastatin or its pharmaceutically acceptable salts, esters, hydrates or solvates, and ezetimibe or its pharmaceutically acceptable salts, esters, hydrates or solvates, wherein each tablet layer only contains one of these active substances and the weight ratio of the individual layers is 1:2 to 2:1 (including the limit values), and wherein the ezetimibe layer comprises a glidant, which is stearic acid or its acceptable salts, at a concentration of 0.15 to 0.5% by weight, relative to the weight of the ezetimibe layer, and wherein the rosuvastatin layer is substantially free of basic stabilizing excipients.

10. A two-layer tablet comprising, as the active ingredients, rosuvastatin or its pharmaceutically acceptable salts, esters, hydrates or solvates, and ezetimibe or its pharmaceutically acceptable salts, esters, hydrates or solvates, wherein each tablet layer only comprises one of these active substances and the mutual weight ratio of the individual layers is 1:2 to 2:1 (including the limit values) and wherein the ezetimibe layer is substantially free of cellulose and its derivatives, or wherein the ezetimibe layer comprises cellulose and its derivatives in the extragranular phase only (preferably microcrystalline cellulose) at a concentration of up to 10.5% by weight, incl. the limit values, relative to the weight of the ezetimibe layer, and wherein the rosuvastatin layer is substantially free of basic stabilizing auxiliary substances.

11. A two-layer tablet comprising, as the active ingredients, rosuvastatin or its pharmaceutically acceptable salts, esters, hydrates or solvates, and ezetimibe or its pharmaceutically acceptable salts, esters, hydrates or solvates, wherein each tablet layer only contains one of these active substances and the weight ratio of the individual layers is 1:2 to 2:1 (including the limit values), and wherein the ezetimibe layer comprises a glidant, which is stearic acid or its acceptable salts, at a concentration of 0.15 to 0.5% by weight, relative to the weight of the ezetimibe layer, and wherein the ezetimibe layer is substantially free of cellulose and its derivatives, or wherein the ezetimibe layer comprises cellulose and its derivatives in the extragranular phase only (preferably microcrystalline cellulose) at a concentration of up to 10.5% by weight, incl. the limit values, relative to the weight of the ezetimibe layer, and wherein the rosuvastatin layer is substantially free of basic stabilizing excipients.

12. A production method of a two-layer tablet according to any one of embodiments 1-11 of the invention.

13. A production method of a two-layer tablet according to any one of the embodiments 1-12 of the invention, wherein the ezetimibe layer is produced by means of wet granulation with water as a wetting agent and the rosuvastatin layer is made by direct mixing and direct compression, the ratio of the compression pressures being in the ratio range of 1:2 to 1:10.

These embodiments bring an unexpected effect on stability of the composition and improvement of release rate and biological availability of the active substances from the composition, solving the problems concerning uneven contents of individual active substances in the tablet layers and undesired abrasion of tablets during the production.

EXAMPLES

Figure 1:
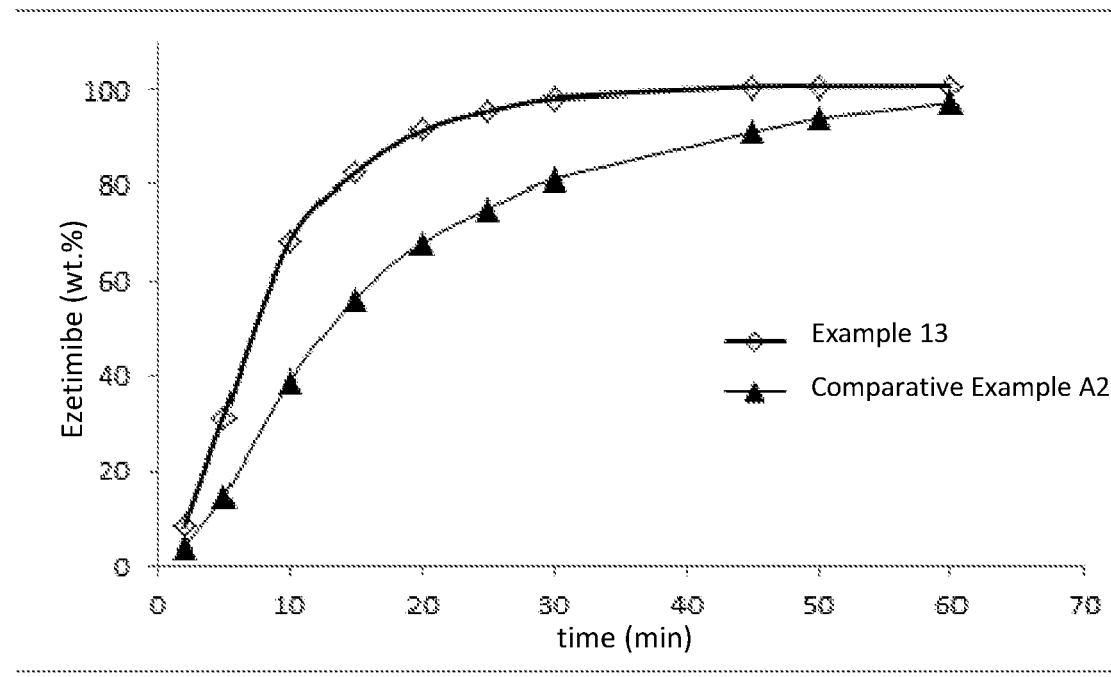
FIG. 1: The dissolution profile of releasing of ezetimibe from a two-layer tablet according to the invention (example 13) as compared to the tablet of Comparative Example A

The embodiment examples below are only provided to illustrate and to explain the invention and are not in any case intended to restrict the protection scope, which is only delimited by the wording of the patent claims. Any other modifications of the composition or production methods are possible if they are implemented in line with maintaining the stability of the composition and the dissolution profile of both the active substances.

Examples of a Stable Formulation of the Ezetimibe Layer

In all the Examples 1 to 6 the tableting blend for the ezetimibe layer was prepared by wet granulation with water as the granulating wetting agent.

Example 1

| Substance name | Function | Composition (mg/tbl) |
|---|---|---|
| Granulate | | |
| Ezetimibe | active ingredient | 10.0 |
| Lactose monohydrate | filler | 141.0 |
| Sodium salt of croscarmellose | disintegrant | 12.0 |
| Sodium lauryl sulphate | surfactant | 4.0 |
| Povidone 25 | binder | 8.0 |
| Extragranular phase | | |
| Microcrystalline cellulose | filler, binder | 20.0 |
| Sodium salt of croscarmellose | disintegrant | 4.0 |
| Magnesium stearate | glidant | 1.0 |
| Layer - total: | | 200.0 |

Example 2

| Substance name | Function | Composition (mg/tbl) |
|---|---|---|
| Granulate | | |
| Ezetimibe | active ingredient | 10.0 |
| Lactose monohydrate | filler | 137.0 |
| Sodium salt of carboxymethyl starch | disintegrant | 14.0 |
| Sodium stearyl sulphate | surfactant | 4.0 |
| Hydroxypropyl methylcellulose (Methocel E5) | binder | 8.0 |
| Extragranular phase | | |
| Microcrystalline cellulose | filler, binder | 20.4 |
| Sodium salt of carboxymethyl starch | disintegrant | 6.0 |
| Magnesium stearate | glidant | 0.6 |
| Layer - total: | | 200.0 |

Example 3

| Substance name | Function | Composition (mg/tbl) |
|---|---|---|
| Granulate | | |
| Ezetimibe | active ingredient | 10.0 |
| Mannitol | filler | 141.0 |
| Sodium salt of croscarmellose | disintegrant | 12.0 |
| Sodium lauryl sulphate | surfactant | 4.0 |
| Povidone 25 | binder | 8.0 |
| Extragranular phase | | |
| Microcrystalline cellulose | filler, binder | 20.7 |
| Sodium salt of croscarmellose | disintegrant | 4.0 |
| Calcium stearate | glidant | 0.3 |
| Layer - total: | | 200.0 |

Example 4

| Substance name | Function | Composition (mg/tbl) |
|---|---|---|
| Granulate | | |
| Ezetimibe | active ingredient | 10.0 |
| Lactose monohydrate | filler | 161.4 |
| Sodium salt of croscarmellose | disintegrant | 12.0 |
| Sodium lauryl sulphate | surfactant | 4.0 |
| Hydroxypropyl methylcellulose (Methocel E5) | binder | 8.0 |
| Extragranular phase | | |
| Microcrystalline cellulose | filler, binder | — |
| Sodium salt of croscarmellose | disintegrant | 4.0 |
| Aluminum stearate | glidant | 0.6 |
| Layer - total: | | 200.0 |

Example 5

| Substance name | Function | Composition (mg/tbl) |
|---|---|---|
| Granulate | | |
| Ezetimibe | active ingredient | 10.0 |
| Mannitol | filler | 141.0 |
| Sodium salt of croscarmellose | disintegrant | 12.0 |
| Sodium lauryl sulphate | surfactant | 4.0 |
| Povidone 25 | binder | 8.0 |
| Extragranular phase | | |
| Microcrystalline cellulose | filler, binder | 20.0 |
| Sodium salt of croscarmellose | disintegrant | 4.0 |
| Stearic acid | glidant | 1.0 |
| Layer - total: | | 200.0 |

Example 6

| Substance name | Function | Composition (mg/tbl) |
|---|---|---|
| Granulate | | |
| Ezetimibe | active ingredient | 10.0 |

-continued

| Substance name | Function | Composition (mg/tbl) |
|---|---|---|
| Lactose monohydrate | filler | 161.0 |
| Sodium salt of croscarmellose | disintegrant | 12.0 |
| Sodium lauryl sulphate | surfactant | 4.0 |
| Povidone 25 | binder | 8.0 |
| Extragranular phase | | |
| Microcrystalline cellulose | filler, binder | — |
| Sodium salt of croscarmellose | disintegrant | 4.0 |
| Magnesium stearate | glidant | 1.0 |
| Layer - total: | | 200.0 |

Examples of a Stable Formulation of the Rosuvastatin Layer

In all the Examples 7 to 12 the tableting blend for the rosuvastatin layer was prepared by direct mixing.

Example 7

| Substance name | Function | Composition (mg/tbl) |
|---|---|---|
| Rosuvastatin layer | | |
| Rosuvastatin calcium salt | active ingredient | 41.6 |
| Lactose monohydrate | filler, binder | 244.0 |
| Microcrystalline cellulose | filler, binder | 94.0 |
| Colloidal silicon dioxide | glidant | 2.4 |
| Sodium salt of croscarmellose | disintegrant | 12.0 |
| Magnesium stearate | glidant | 6.0 |
| Layer - total: | | 400.0 |

Example 8

| Substance name | Function | Composition (mg/tbl) |
|---|---|---|
| Rosuvastatin layer | | |
| Rosuvastatin calcium salt | active ingredient | 41.6 |
| Lactose monohydrate | filler, binder | 244.0 |
| Microcrystalline cellulose | filler, binder | 94.0 |
| Talc/talcum powder | glidant | 2.4 |
| Sodium salt of croscarmellose | disintegrant | 12.0 |
| Magnesium stearate | glidant | 6.0 |
| Layer - total: | | 400.0 |

Example 9

| Substance name | Function | Composition (mg/tbl) |
|---|---|---|
| Rosuvastatin layer | | |
| Rosuvastatin calcium salt | active ingredient | 41.6 |
| Mannitol | filler, binder | 244.0 |
| 24Microcrystalline cellulose | filler, binder | 94.0 |
| Colloidal silicon dioxide | glidant | 2.4 |

-continued

| Substance name | Function | Composition (mg/tbl) |
|---|---|---|
| Sodium salt of croscarmellose | disintegrant | 12.0 |
| Aluminum stearate | glidant | 6.0 |
| Layer - total: | | 400.0 |

Example 10

| Substance name | Function | Composition (mg/tbl) |
|---|---|---|
| Rosuvastatin layer | | |
| Rosuvastatin calcium salt | active ingredient | 41.6 |
| Mannitol | filler, binder | 240.0 |
| Microcrystalline cellulose | filler, binder | 94.0 |
| Colloidal silicon dioxide | glidant | 2.4 |
| Sodium salt of carboxymethyl starch | disintegrant | 16.0 |
| Calcium stearate | glidant | 6.0 |
| Layer - total: | | 400.0 |

Example 11

| Substance name | Function | Composition (mg/tbl) |
|---|---|---|
| Rosuvastatin layer | | |
| Rosuvastatin calcium salt | active ingredient | 20.8 |
| Lactose monohydrate | filler, binder | 122.0 |
| Microcrystalline cellulose | filler, binder | 47.0 |
| Colloidal silicon dioxide | glidant | 1.2 |
| Sodium salt of croscarmellose | disintegrant | 6.0 |
| Magnesium stearate | glidant | 3.0 |
| Layer - total: | | 200.0 |

Example 12

| Substance name | Function | Composition (mg/tbl) |
|---|---|---|
| Rosuvastatin layer | | |
| Rosuvastatin calcium salt | active ingredient | 10.4 |
| Lactose monohydrate | filler, binder | 61.0 |
| Microcrystalline cellulose | filler, binder | 23.5 |
| Colloidal silicon dioxide | glidant | 0.6 |
| Sodium salt of croscarmellose | disintegrant | 3.0 |
| Magnesium stearate | glidant | 1.5 |
| Layer - total: | | 100.0 |

Stable Formulation of a Two-Layer Tablet Comprising an Ezetimibe Layer and a Rosuvastatin Layer

Examples 13-15

| Substance name | Composition (mg/tbl) | | |
|---|---|---|---|
| | Example 13 | Example 14 | Example 15 |
| Ezetimibe layer | according to Example 1 | according to Example 1 | according to Example 1 |
| Rosuvastatin layer | according to Example 7 | according to Example 11 | according to Example 12 |
| Tablet core - total: | 600.0 | 400.0 | 300.0 |
| Coating layer | | | |
| Hydroxypropyl methylcellulose | 10.45 | 6.97 | 5.23 |
| Polyethylene glycol 6000 | 1.50 | 1 | 0.75 |
| Titanium dioxide | 1.20 | 0.8 | 0.6 |
| Talc | 1.80 | 1.2 | 0.9 |
| Red iron oxide | 0.05 | — | — |
| Yellow iron oxide | — | 0.03 | — |
| Tablet - total: | 615.0 | 410.0 | 307.48 |

Abrasion, determined using the method according to the European Pharmacopoeia, was less than 0.2% for Examples 13-15.

During the dissolution test, more than 90% by weight of the declared amount of ezetimibe was released from the tablets after 30 minutes:

| Test | Example 13 | Example 14 | Example 15 |
|---|---|---|---|
| Disintegration time of the two-layer tablet | 3 min | 4 min | 3 min |
| Released ezetimibe after 30 min (% by weight, average value of 10 tablets) | 98.3% | 94.7 | 97.6% |
| Released ezetimibe after 30 min (% by weight, minimum measured value of 10 tablets) | 96.5% | 90.7% | 94.3 |
| Released rosuvastatin after 30 min (% by weight, average value of 10 tablets) | 97.6% | 99.6% | 99.6% |
| Released rosuvastatin after 30 min (% by weight, minimum measured value of 10 tablets) | 95.6% | 98.3% | 95.7% |

| Test | Example 13 | Example 14 | Example 15 |
|---|---|---|---|
| Content of ezetimibe after the production, average value of 10 tablets (minimum and maximum measured value) | 10.2 mg (9.9-10.3 mg) | 10.1 mg (10.0-10.2 mg) | 10.2 mg (9.9-10.2 mg) |
| Content of rosuvastatin after the production, average value of 10 tablets (minimum and maximum measured value) | 40.2 mg (39.3-40.4 mg) | 20.1 mg (19.8-20.2 mg) | 10.2 mg (9.8-10.3 mg) |

Examples 16-18

| Substance name | Composition (mg/tbl) | | |
|---|---|---|---|
| | Example 16 | Example 17 | Example 18 |
| Ezetimibe layer | according to Example 2 | according to Example 4 | according to Example 5 |
| Rosuvastatin layer | according to Example 8 | according to Example 11 | according to Example 12 |
| Tablet core - total: | 600.0 | 400.0 | 300.0 |
| Coating layer | | | |
| Hydroxypropyl methylcellulose | 10.45 | 6.97 | 5.23 |
| Polyethylene glycol 6000 | 1.50 | 1 | 0.75 |
| Titanium dioxide | 1.20 | 0.8 | 0.6 |
| Talc | 1.80 | 1.2 | 0.9 |
| Red iron oxide | 0.05 | — | — |
| Yellow iron oxide | — | 0.03 | — |
| Tablet - total: | 615.0 | 410.0 | 307.48 |

Abrasion, determined using the method according to the European Pharmacopoeia, was less than 0.2% for Examples 16-18.

| Test | Example 16 | Example 17 | Example 18 |
|---|---|---|---|
| Disintegration time of the two-layer tablet | 3 min | 3 min | 4 min |
| Released ezetimibe after 30 min (% by weight, average value of 10 tablets) | 96.2% | 93.4 | 97.1% |
| Released ezetimibe after 30 min (% by weight, minimum measured value of 10 tablets) | 86.5% | 85.3% | 93.2% |
| Released rosuvastatin after 30 min (% by weight, average value of 10 tablets) | 97.1% | 97.1% | 97.5% |
| Released rosuvastatin after 30 min (% by weight, minimum measured value of 10 tablets) | 96.3% | 93.1% | 96.7% |

Examples 19-21

| Substance name | Example 19 | Example 20 | Example 21 |
|---|---|---|---|
| Ezetimibe layer | according to Example 1 | according to Example 3 | according to Example 6 |
| Rosuvastatin layer | according to Example 9 | according to Example 11 | according to Example 12 |
| Tablet core - total: | 600.0 | 400.0 | 300.0 |
| Coating layer | | | |
| Hydroxypropyl methylcellulose | 10.45 | 6.97 | 5.23 |
| Polyethylene glycol 6000 | 1.50 | 1 | 0.75 |
| Titanium dioxide | 1.20 | 0.8 | 0.6 |
| Talc | 1.80 | 1.2 | 0.9 |
| Red iron oxide | 0.05 | — | — |
| Yellow iron oxide | — | 0.03 | — |
| Tablet - total: | 615.0 | 410.0 | 307.48 |

Abrasion, determined using the method according to the European Pharmacopoeia, was less than 0.2% for Examples 19-21.

| Test | Example 19 | Example 20 | Example 21 |
|---|---|---|---|
| Disintegration time of the two-layer tablet | 5 min | 3 min | 4 min |
| Released ezetimibe after 30 min (% by weight, average value of 10 tablets) | 96.2% | 98.2% | 97.4% |
| Released ezetimibe after 30 min (% by weight, minimum measured value of 10 tablets) | 86.5% | 95.8% | 90.9% |
| Released rosuvastatin after 30 min (% by weight, average value of 10 tablets) | 97.1% | 97.4% | 98.2% |
| Released rosuvastatin after 30 min (% by weight, minimum measured value of 10 tablets) | 96.3% | 94.7% | 96.4% |

COMPARATIVE EXAMPLES

In all the Comparative Examples A to D, the tableting blend for the ezetimibe layer was prepared in the same way as in Examples 1 to 6, i.e. by means of wet granulation with water as the granulation wetting agent, and the tableting blend for the rosuvastatin layer was prepared in the same way as in Examples 7 to 12, i.e. by means of direct mixing. After the compression, coating was applied onto the two-layer tablets in the same way as in Example 13.

Comparative Example A—Magnesium Stearate Contents 1% by Weight and 1.5% by Weight

| Substance name | Composition A1 (mg/tbl) | Composition A2 (mg/tbl) |
|---|---|---|
| Ezetimibe granulate: | | |
| Ezetimibe | 10.0 | 10.0 |
| Lactose monohydrate | 140.0 | 139.0 |
| Sodium salt of croscarmellose | 12.0 | 12.0 |
| Sodium lauryl sulphate | 4.0 | 4.0 |
| Povidone 25 | 8.0 | 8.0 |
| Extragranular phase: | | |
| Microcrystalline cellulose | 20.0 | 20.0 |
| Sodium salt of croscarmellose | 4.0 | 4.0 |
| Magnesium stearate | 2.0 | 3.0 |
| Ezetimibe layer—total: | 200.0 | 200.0 |
| Rosuvastatin layer: | | |
| Rosuvastatin calcium salt | 41.6 | 41.6 |
| Lactose monohydrate | 244.0 | 244.0 |
| Microcrystalline cellulose | 94.0 | 94.0 |
| Colloidal silicon dioxide | 2.4 | 2.4 |
| Sodium salt of croscarmellose | 12.0 | 12.0 |
| Magnesium stearate | 6.0 | 6.0 |
| Rosuvastatin layer—total: | 400.0 | 400.0 |
| Tablet—total: | 600.0 | 600.0 |

| Test | Comparative Example A1 | Comparative Example A2 |
|---|---|---|
| Disintegration time of the two-layer tablet | 4 min | 5 min |
| Released ezetimibe after 30 min (% by weight, average value of 10 tablets) | 84.7% | 81.1% |

| Test | Comparative Example A1 | Comparative Example A2 |
|---|---|---|
| Released ezetimibe after 30 min (% by weight, minimum measured value of 10 tablets) | 79.1% | 77.3% |
| Released rosuvastatin after 30 min (% by weight, average value of 10 tablets) | 97.1% | 97.4% |
| Released rosuvastatin after 30 min (% by weight, minimum measured value of 10 tablets) | 96.3% | 94.7% |

The dissolution profiles of tablet A2 and the tablet in accordance with Example 13 are shown in FIG. 1.

Comparative Example B—Ratio of Layers 1:3 and 3:1

| Substance name | Composition B1 (mg/tbl) | Composition B2 (mg/tbl) |
|---|---|---|
| Ezetimibe granulate: | | |
| Ezetimibe | 10.0 | 10.0 |
| Lactose monohydrate | 90.5 | 224.8 |
| Sodium salt of croscarmellose | 8.0 | 16.0 |
| Sodium lauryl sulphate | 2.7 | 5.3 |
| Povidone 25 | 5.3 | 10.6 |
| Extragranular phase: | | |
| Microcrystalline cellulose | 13.3 | 26.6 |
| Sodium salt of croscarmellose | 2.7 | 5.3 |
| Magnesium stearate | 0.6 | 1.3 |
| Ezetimibe layer—total: | 133.1 | 299.9 |
| Rosuvastatin layer: | | |

| Substance name | Composition B1 (mg/tbl) | Composition B2 (mg/tbl) |
| --- | --- | --- |
| Rosuvastatin calcium salt | 41.6 | 10.4 |
| Lactose monohydrate | 244.0 | 61.0 |
| Microcrystalline cellulose | 94.0 | 23.5 |
| Colloidal silicon dioxide | 2.4 | 0.6 |
| Sodium salt of croscarmellose | 12.0 | 3.0 |
| Magnesium stearate | 6.0 | 1.5 |
| Rosuvastatin layer-total: | 400.0 | 100.0 |
| Tablet-total: | 533.1 | 399.9 |

Abrasion, determined using the method according to the European Pharmacopoeia, was 4% for composition B1 and 6% for composition B2.

| Test | Comparative Example B1 | Comparative Example B2 |
| --- | --- | --- |
| Content of ezetimibe after the production (average value of 10 tablets, minimum and maximum measured value) | 10.2 mg (9.3-10.6 mg) | 10.1 mg (9.1-10.7 mg) |
| Content of rosuvastatin after the production (average value of 10 tablets, minimum and maximum measured value) | 39.9 mg (37.6-42.4 mg) | 40.2 mg (38.0-42.7 mg) |

Comparative Example C—Microcrystalline Cellulose in the Intragranular Phase of the Ezetimibe Layer

| Substance name | Function | Composition (mg/tbl) |
| --- | --- | --- |
| Granulate | | |
| Ezetimibe | active ingredient | 10.0 |
| Lactose monohydrate | filler | 131.0 |
| Microcrystalline cellulose | filler, binder | 10.0 |
| Sodium salt of croscarmellose | disintegrant | 12.0 |
| Sodium lauryl sulphate | surfactant | 4.0 |
| Povidone 25 | binder | 8.0 |
| Extragranular phase | | |
| Microcrystalline cellulose | filler, binder | 20.0 |
| Sodium salt of croscarmellose | disintegrant | 4.0 |
| Magnesium stearate | glidant | 1.0 |
| Layer - total: | | 200.0 |
| Rosuvastatin layer | | |
| Rosuvastatin calcium salt | active ingredient | 41.6 |
| Lactose monohydrate | filler, binder | 244.0 |
| Microcrystalline cellulose | filler, binder | 94.0 |
| Colloidal silicon dioxide | glidant | 2.4 |
| Sodium salt of croscarmellose | disintegrant | 12.0 |
| Magnesium stearate | glidant | 6.0 |
| Layer - total: | | 400.0 |

| Test | Comparative Example C |
| --- | --- |
| Disintegration time of the two-layer tablet | 7 min |
| Released ezetimibe after 30 min (% by weight, average value of 10 tablets) | 82.6% |
| Released ezetimibe after 30 min (% by weight, minimum measured value of 10 tablets) | 77.3% |
| Released rosuvastatin after 30 min (% by weight, average value of 10 tablets) | 98.2% |
| Released rosuvastatin after 30 min (% by weight, minimum measured value of 10 tablets) | 96.4 |

Figure 2:
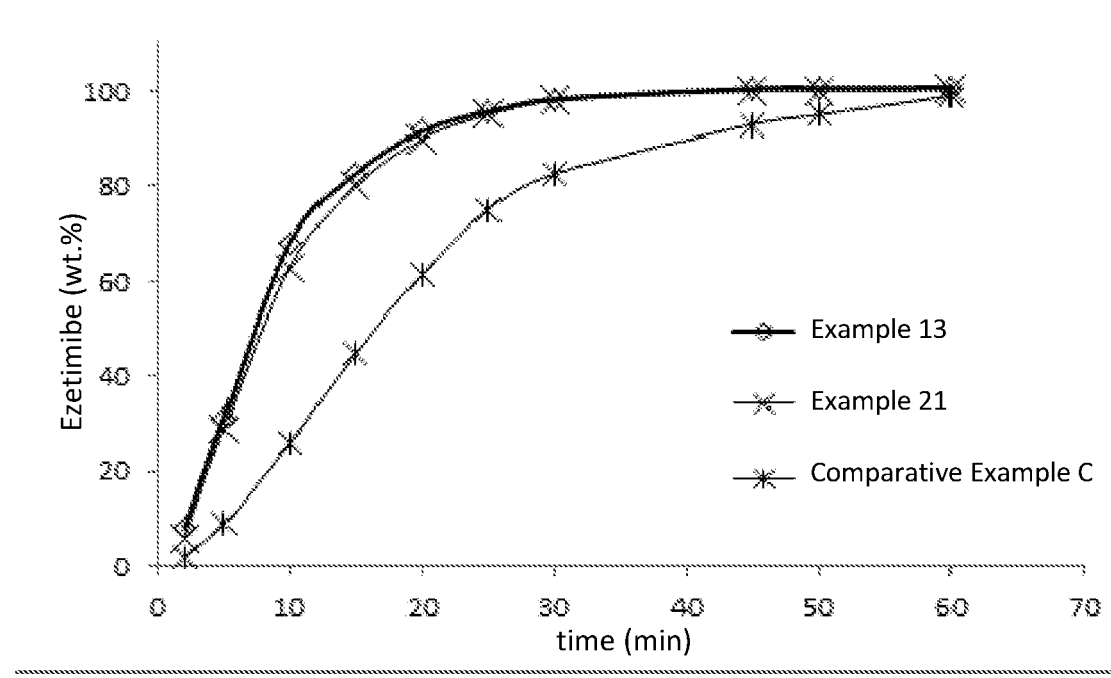
FIG. 2: The dissolution profile of releasing of ezetimibe from a two-layer tablet according to the invention (example 13) as compared to the tablet of Comparative Example C

The dissolution profile of releasing of ezetimibe was measured and compared to the dissolution profile of the tablet in accordance with Example 13 and 21. The dissolution profile of the tablet in accordance with Comparative Example C and the tablet in accordance with Example 13 and 21 are shown in FIG. 2.

Comparative Example D—Stabilization of the Rosuvastatin Layer with Calcium Hydrogen Phosphate

| Substance name | Composition (mg/tbl) |
| --- | --- |
| Ezetimibe granulate: | |
| Ezetimibe | 10.0 |
| Lactose monohydrate | 141.0 |
| Sodium salt of croscarmellose | 12.0 |
| Sodium lauryl sulphate | 4.0 |
| Povidone 25 | 8.0 |
| Extragranular phase: | |
| Microcrystalline cellulose | 20.0 |
| Sodium salt of croscarmellose | 4.0 |
| Magnesium stearate | 1.0 |
| Ezetimibe layer - total: | 200.0 |
| Rosuvastatin layer: | |
| Rosuvastatin calcium salt | 41.6 |
| Lactose monohydrate | 224.0 |
| Calcium hydrogen phosphate | 20 |
| Microcrystalline cellulose | 94.0 |
| Colloidal silicon dioxide | 2.4 |
| Sodium salt of croscarmellose | 12.0 |
| Magnesium stearate | 6.0 |
| Rosuvastatin layer - total: | 400.0 |
| Coating layer: | |
| Hydroxypropyl methylcellulose | 10.45 |
| Polyethylene glycol 6000 | 1.50 |
| Titanium dioxide | 1.20 |
| Talc | 1.80 |
| Red iron oxide | 0.05 |
| Yellow iron oxide | — |
| Tablet - total: | 615.0 |

Two-layer tablets according to Comparative Example D, stabilized with calcium hydrogen phosphate, and two-layer tablets according to Example 13 were exposed to a stability test at the conditions of 40° C. and 75% relative humidity for 6 months. The results show that the two-layer tablet according to the invention is as stable as the two-layer tablet stabilized with calcium hydrogen phosphate.

| Test | Comparative Example 2 | Example 13 |
|---|---|---|
| Total contents of impurities of ezetimibe (average value of 10 tablets, minimum and maximum measured value) | 0.06% (<0.05-0.06%) | <0.05% (<0.05-0.06%) |
| Total contents of impurities of rosuvastatin (average value of 10 tablets, minimum and maximum measured value) | 0.28% 0.20-0.32 | 0.31 (0.24-0.37%) |

Methods Used
　Unless specified otherwise, methods according to Ph. Eur (European Pharmacopoeia) were used.
Variability of the Contents of the Active Ingredients, Uniformity of the Contents, Abrasion, Disintegration Time, Strength
　according to Ph. Eur (European Pharmacopoeia)
Dissolution Measurements
　A device with stirrers according to Ph. Eur. (European Pharmacopoeia)
　900 ml, phosphate buffer, having pH 7.0±0.05 with 0.5% of sodium lauryl sulphate, 75 rpm
　HPLC chromatography with a column detector with a UV or PDA detector, column Kinetex 2.6μ, C18, 30×4.60 mm or its equivalent, mobile phase 0.1% of phosphoric acid:methanol (42:58 v/v), solvent acetonitrile:water (60:40, v/v), detection 242 nm
Stability
　stability test, storage at the conditions of 40° C. and 75% relative humidity for 6 months
　gradient elution method on HPLC chromatography with a UV (PDA) detector, column Gemini C6-Phenyl, 3 μm, 150×4.6 mm or its equivalent, mobile phase 1.0 ml of phosphoric acid per 1000 ml of water (constituent A) and methanol (constituent B) in the gradient program as specified in the table below, detection 245 nm

| Time (min) | Constituent A (% v/v) | Constituent B (% v/v) |
|---|---|---|
| 0 | 45 | 55 |
| 11.0 | 40 | 60 |
| 14.0 | 25 | 75 |
| 19.0 | 25 | 75 |
| 19.5 | 45 | 55 |
| 23.0 | 45 | 55 |

Uniformity, Variability of the Contents
　HPLC chromatography with a column thermostat and UV detector, column Gemini C6-Phenyl, 3 μm, 150×4.6 mm (Phenomenex) or its equivalent, mobile phase 0.085% of phosphoric acid:methanol (35:65, v/v), detection 245 nm.

The invention claimed is:
1. A two-layer oral tablet comprising:
　(a) rosuvastatin or its pharmaceutically acceptable salts, esters, hydrates or solvates;
　(b) ezetimibe or its pharmaceutically acceptable salts, esters, hydrates or solvates;
wherein the tablet comprises one ezetimibe layer and one rosuvastatin layer;
wherein said ezetimibe layer comprises a granulate and an extragranulate phase;
wherein the granulate comprises ezetimibe or its pharmaceutically acceptable salts, esters, hydrates or solvates;
wherein the extragranulate phase comprises stearic acid or its acceptable salts as a glidant at a concentration of 0.15 to 0.5% by weight, including the limit values, relative to the weight of the ezetimibe layer, and at least one further pharmaceutically acceptable excipient comprising a filler, a binder, or a disintegrant; and
wherein said rosuvastatin layer consists of rosuvastatin or its pharmaceutically acceptable salt, ester, hydrate or solvate, and at least one pharmaceutically acceptable excipient, wherein said pharmaceutically acceptable excipient(s) are non-basic, and
wherein the rosuvastatin layer does not contain a basic excipient.
2. The two-layer oral tablet according to claim 1, wherein the stearic acid or its acceptable salts comprise magnesium stearate, calcium stearate, or aluminum stearate.
3. The two-layer oral tablet according to claim 1, wherein the weight ratio of the ezetimibe layer and rosuvastatin layer is in the range from 1:2 to 2:1, including the limit values.
4. The two-layer oral tablet according to claim 1, wherein the granulate of the ezetimibe layer comprises ezetimibe or its pharmaceutically acceptable salt, ester, hydrate or solvate, and at least one pharmaceutically acceptable excipient comprising a filler, a binder, a disintegrant, or a surfactant.
5. The two-layer oral tablet according to claim 1, wherein the granulate of the ezetimibe layer is free of microcrystalline cellulose and wherein the extragranulate layer comprises microcrystalline cellulose.
6. The two-layer oral tablet according to claim 1, wherein the extragranular phase of the ezetimibe layer comprises microcrystalline cellulose, at a concentration of up to 10.5% by weight, including the limit values, relative to the weight of the ezetimibe layer.
7. The two-layer oral tablet according to claim 1, wherein the ezetimibe layer comprises:
　a filler or a combination of fillers comprising lactose, glucose, calcium carbonate, calcium phosphate, starch, or sugar alcohols;
　a binder or a combination of binders comprising water-soluble polymers or water-soluble cellulose derivatives, said water-soluble cellulose derivatives comprising methylcellulose, hydroxyethyl cellulose, hydroxypropyl cellulose or hydroxypropyl methylcellulose;
　a disintegrant or a combination of disintegrants comprising sodium salt of croscarmellose, sodium salt of carboxymethyl starch, crospovidone, or alginates; or
　a surfactant or a combination of surfactants comprising block copolymers of ethylene oxide and propylene oxide, alkyl sulphates, alkyl aryl sulfonates, polyethylene glycols, or polysorbates.
8. The two-layer oral tablet according to claim 1, wherein the at least one pharmaceutically acceptable non-basic excipient in the rosuvastatin layer consists of:
　a filler or a combination of fillers comprising lactose or its monohydrate, glucose, cellulose, starch, or sugar alcohols;
　a binder or a combination of binders comprising polyvinylpyrrolidone, microcrystalline cellulose, water-soluble cellulose, or sugar alcohols;
　a disintegrant or a combination of disintegrants comprising sodium salt of croscarmellose, sodium salt of carboxymethyl starch, crospovidone or alginates;
　a glidant or a combination of glidants comprising colloidal silicon dioxide, maize starch, talc, polyethylene oxide, sodium stearyl fumarate, or stearic acid or its acceptable salts; or
　any combination thereof.

9. The two-layer oral tablet according to claim 1, wherein the tablet contains 10 mg of ezetimibe or the corresponding amount of its pharmaceutically acceptable salt, ester, hydrate or solvate, and 5 to 45 mg of rosuvastatin or the corresponding amount of its pharmaceutically acceptable salt, ester, hydrate or solvate.

10. A method of preparation of a two-layer oral tablet comprising rosuvastatin or its pharmaceutically acceptable salts, esters, hydrates or solvates, and ezetimibe or its pharmaceutically acceptable salts, esters, hydrates or solvates, and pharmaceutically acceptable excipients, and consisting of one ezetimibe layer and one rosuvastatin layer, wherein the method comprises the steps a) to e):
  a) ezetimibe or its pharmaceutically acceptable salt, together with at least one first pharmaceutically acceptable excipient which is other than microcrystalline cellulose, is granulated with the use of water as a wetting agent,
  b) the obtained granules of ezetimibe are mixed with at least one second pharmaceutically acceptable excipient, the at least one second pharmaceutically acceptable excipient being a glidant, which is stearic acid or its acceptable salts, at a concentration of 0.15 to 0.5% by weight, including the limit values, relative to the weight of the ezetimibe layer, and at least one other pharmaceutically acceptable excipient selected from a group comprising a filler, a binder and a disintegrant;
  c) rosuvastatin or its pharmaceutically acceptable salt, is mixed together with at least one pharmaceutically acceptable excipient, said excipient(s) being non-basic, wherein the rosuvastatin layer does not contain a basic excipient,
  d) the obtained tableting blend of ezetimibe and rosuvastatin is compressed into two-layer tablets,
  e) coating is optionally applied onto the obtained two-layer tablets.

11. The method according to claim 10, wherein the at least one first pharmaceutically acceptable excipient in step a) is selected from a group comprising a filler, a binder, a disintegrant, a surfactant or any combinations thereof.

12. The method according to claim 10, wherein the mixture of ezetimibe with at least one first pharmaceutically acceptable excipient in step a) is wetted with the use of water and the obtained mixture is processed into granulate by means of fluid granulation.

13. The method according to claim 10, wherein the at least one second pharmaceutically acceptable excipient in step b) in the extragranular phase is magnesium stearate, calcium stearate or aluminum stearate.

14. The method according to claim 10, wherein the second pharmaceutically acceptable excipients in step b) in the extragranular phase comprise microcrystalline cellulose, contained in a total concentration of up to 10.5% by weight, including the limit values, relative to the weight of the ezetimibe layer; or the second pharmaceutically acceptable excipients are free of microcrystalline cellulose.

15. The method according to claim 10, wherein the at least one pharmaceutically acceptable non-basic excipient in step c) is selected from a group comprising:
  a filler or a combination of fillers, selected from the group comprising lactose or its monohydrate, glucose, cellulose and its derivatives, starch, and sugar alcohols;
  a binder or a combination of binders selected from a group comprising polyvinylpyrrolidone, microcrystalline cellulose, water-soluble cellulose derivatives, and sugar alcohols;
  a disintegrant or a combination of disintegrants selected from a group comprising sodium salt of croscarmellose, sodium salt of carboxymethyl starch, crospovidone, and alginates;
  a glidant or combination of glidants, selected from a group comprising colloidal silicon dioxide, maize starch, talc, polyethylene oxide, sodium stearyl fumarate, and stearic acid or its acceptable salts; and any combination thereof.

* * * * *